United States Patent [19]

Grivsky

[11] 4,190,674
[45] Feb. 26, 1980

[54] 3-FLUORO-N-CYCLOPROPYLCINNAMIDE

[75] Inventor: Eugene M. Grivsky, Chapel Hill, N.C.

[73] Assignee: Burroughs Wellcome Co., Research Triangle Park, N.C.

[21] Appl. No.: 916,275

[22] Filed: Jun. 16, 1978

Related U.S. Application Data

[63] Continuation-in-part of Ser. No. 712,134, Aug. 6, 1976, abandoned, and a continuation-in-part of Ser. No. 820,300, Jul. 29, 1977, abandoned.

[30] Foreign Application Priority Data

Jan. 27, 1977 [GB] United Kingdom ............... 4168/77

[51] Int. Cl.$^2$ .................. C07C 103/76; A61K 31/165
[52] U.S. Cl. .................. 424/324; 260/558 R; 260/558 D
[58] Field of Search .................. 260/558 R, 558 D; 424/324

[56] References Cited

U.S. PATENT DOCUMENTS

| | | | |
|---|---|---|---|
| 3,659,014 | 4/1972 | Bayssat et al. | 424/324 |
| 4,041,071 | 8/1977 | Grivsky | 260/558 R |
| 4,053,635 | 10/1977 | Gorini et al. | 260/558 R X |
| 4,091,112 | 5/1978 | Grivsky | 424/324 |

FOREIGN PATENT DOCUMENTS 832283 2/1976 Belgium .
663903 12/1951 United Kingdom .

OTHER PUBLICATIONS

Szilazyi et al., Acta. Pharm. Hung. 39:66–73 (1969).
Heyningen et al., J. Med. Chem., vol. 9, pp. 675–681 (1966).
Papa et al., J. Amer. Chem. Soc., vol. 72, pp. 3885–3886 (1950).
Shinohara et al., CA 83:109795c (1975).

*Primary Examiner*—Thomas A. Waltz
*Attorney, Agent, or Firm*—Donald Brown

[57] ABSTRACT

Cinnamamides of formula (I),

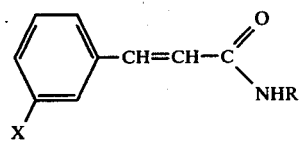

wherein X is fluoro, chloro, bromo, iodo or trifluoromethyl and R is cycloalkyl or cycloalkyl alkyl, have anticonvulsant properties. The compound trans-3-fluoro-(N-cyclopropyl)cinnamamide is also useful as a muscle relaxant.

19 Claims, No Drawings

3-FLUORO-N-CYCLOPROPYLCINNAMIDE

This application is a continuation-in-part of U.S. patent application Ser. No. 712,134 filed Aug. 6, 1976, and Ser. No. 820,300 filed July 29, 1977 both now abandoned.

This invention is concerned with chemicals which have valuable pharmacological properties. In particular, the invention concerns cinnamamides, their synthesis, pharmaceutical preparations containing them, and their use in medicine.

It has been found that the cinnamamides of formula (I), as defined below, have anti-convulsant activity in mammals as is shown by their effects upon mice when administered to them in established pharmacological tests. These tests are:

1. Maximal Electroschock Test (MES) in mice, a method described by Woodbury and Davenport, Arch int. Pharmacodyn. Ther. 92, P. 97-107 (1952).
2. Metrazol Seizure Test (MET) in mice, a method described by Swinyard, Brown and Goodman, J. Pharmacol. Exp. Therap. 106, 319-330 (1952).

In formula (I)

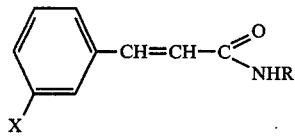

(I)

X is chlorine, bromine, iodine, fluorine or trifluoromethyl and R is cycloalkyl having 3 to 8 carbon atoms or cycloalkyalkyl wherein the cycloalkyl moiety has 3 to 8 carbon atoms and the alkyl moiety has 1 to 3 carbon atoms.

The trans configuration of the compounds of formula (I) is preferred, and as subclasses among the compounds within the scope of this formula may be mentioned:
(a) those wherein R is cycloalkyalkyl; and
(b) those wherein R is cycloalkyl;
and as a group within the latter subclass may be mentioned those wherein R is cyclopropyl. The most preferred anticonvulsant compound of Formula (I) is Trans 3-chloro-N-cyclopropylcinnamamide.

Among the compounds within formula (I) may specifically be mentioned is trans:
3-fluoro-N-cyclopropylcinnamamide;
3-chloro-N-cyclopropylcinnamamide;
3-bromo-N-cyclopropylcinnamamide;
3-iodo-N-cyclopropylcinnamamide;
3-trifluoromethyl-N-cyclopropylcinnamamide;
3-chloro-N-cyclopentylcinnamamide;
3-bromo-N-cyclopentylcinnamamide;
3-bromo-N-cycloheptylcinnamamide; and
3-bromo-N-cyclohexylmethylcinnamamide.

The compounds of formula (I) may be made by any method known for the synthesis of cinnamamides of analogous structure. For example they may be prepared by the acylation of an amine $RNH_2$ [wherein R is as defined in formula (I) above] by the corresponding acid of formula (II): $m-X-PhCH=CHCO_2H$ (wherein X has the meaning given for formula (I) or a reactive derivative thereof such as a thioester or an ester (e.g. an alkyl ester or thioester where the alkyl has e.g. 1 to 4 carbon atoms), an amide, an acid halide (e.g. an acid chloride) or an acid anhydride. A wide variety of reaction conditions may be employed depending upon the nature of the acylating agent, but in general the reactants may be refluxed together, preferably in an inert liquid medium such as ether, benzene, toluene or cyclohexane.

A most convenient method of synthesis is to react the acid chloride with the appropriate amine. Preferably one equivalent of the halide should be used with two or more equivalents of the amine, but the molar excess of the amine may be replaced by another base such as triethylamine, pyridine, dimethylaniline, or potassium or sodium carbonate. A wide variety of polar or nonpolar liquid media may be used including water, alkanols such as methanol, ethanol, etc., ether, dioxane, benzene, toluene, xylene, protroleum ether, cyclohexane, tetrahydrofuran, chloroform and carbon tetrachloride. A wide range of temperature conditions may be employed, for example from $-10°$ C. to the reflux termperature of the reaction mixture.

The compounds of formula (I) may be further prepared directly from the corresponding alcohol or aldehyde of formula (III) and (IV) at a temperature below $10°$ C.

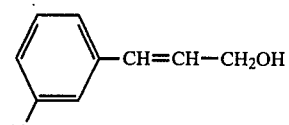

(III)

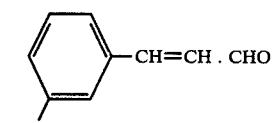

(IV)

wherein X has the meaning in formula (I), by reaction with the appropriate amine $RNH_2$ in the presence of nickel peroxide and an inert liquid medium such as ether, benzene, tetrahydrofuran, or a petroleum hydrocarbon.

The compounds of formula (I) may also be made by the reaction of an amide of formula (V): R.NE.W wherein W is a leaving group, for example —CO.H (a formamide), —CO. alkyl where the alkyl has e.g. 1 to 4 carbon atoms (an amide), —CONH$_2$ (urea), —COO. alkyl (urethane having 1-4 carbon atoms in the alkyl group), with an acid of formula (II) or a reactive derivative thereof, for example the acid anhydride or halide. When the anhydride is used, a catalytic amount of sulphuric acid is preferably included. The reactants are conveniently heated together in a liquid medium.

In a further method for making a compound of formula (I) water, a hydrogen halide or molecular halogen is eliminated from a compound of formula (VI)

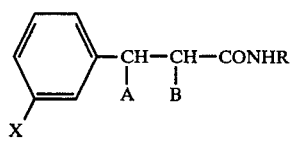

(VI)

wherein A and B are the same and each is halo or one of A and B is halo or hydroxy and the other is hydrogen, and X and R have the meaning given in formula (I) above. For example, the elimination of water from the a- or β-hydroxy compounds of formula (VI) may be effected by reaction with a dehydrating agent such as a base (e.g. aqueous sodium hydroxide) or concentrated sulphuric or polyphosphoric acid. The monohalo intermediates may be treated with a base (e.g., potassium hydroxde or dimethylaniline) or merely heated to release the hydrogen halide. The dihalo halo intermediates may be reduced, for example with zinc and ethanol or converted to the diiode compounds by treatment with potassium iodide with subsequent release of molecular iodine.

The intermediate acids of formula (II) may be made by classical organic synthetic methods such as the Perkin synthesis, the Reformatsky reaction and the Knoevenagel condensation.

The compounds of formula (I) may be used for the treatment or prophylaxis of convulsions of mammals such as mice, dogs and cats, more importantly of man. In particular they may be used in the treatment of grand mal, petit mal, psychomotor epilepsy and focal seizures at a dose of 2 to 200 mg/kg of body weight per day. The optimum dose of course will vary with the nature of the compound, the condition of the patient and the route of administration, but the preferred dose is in the range of 20 to 60 mg/kg, most conveniently 30 to 50 mg/kg body weight, per day. Administration of the desired daily dose is preferably in three divided doses. For example, convenient forms of administration as an anticonvulsant include tablets each containing from 100 to 500 mg of a compound of formula (I).

For use in medicine the compounds of formula (I) may be administered as a pure chemical but are preferably presented with an acceptable carrier therefor as a pharmaceutical composition. The carrier must of course be 'acceptable' in the sense of being compatible with the other ingredients of the composition and not deleterious to the recipient of the composition. The carrier may be a solid or a liquid or a mixture of solid and liquid substances, and is preferably formulated with a compound of formula (I) as a unit-dose composition, for example a tablet, capsule or sachet for oral administration or a suppository for rectal administration. Other pharmaceutically active substances may also be present in compositions of the present invention, and the composition may be formulated by any of the well-known techniques of pharmacy consisting basically of admixture of its components. Unit-dose compositions as an anticonvulsant, for oral, rectal or parenteral administration (vid. inf.), conveniently contain a compound of formula (I) in an amount in the range 100 to 500 mg.

For oral administration, fine powders or granules of the compounds may contain diluents and dispersing and surface active agents, and may be presented in a draught in water or in a syrup; in capsules or cachets in the dry state or in an aqueous or non-aqueous suspension, when a suspending agent may also be included; in tablets, preferably made from granules of the active ingredient with a diluent, by compression with binders and lubricants; or in a suspension in water or a syrup or an oil or in a water/oil emulsion, when flavouring, preserving, suspending, thickening an emulsifying agents may also be included. The granules or the tablets may be coated, and the tablets may be scored.

For parenteral administration (by intramuscular or intreperitoneal injection), the compounds may be presented in unit dose or multi-dose containers in aqueous or non-aqueous injection solutions which may contain antioxidants, buffers, bacteriostats and solutes which render the compounds isotonic with the blood; or in aqueous or non-aqueous suspensions when suspending agents and thickening agents may also be included; extemporaneous injection solutions and suspensions may be made from sterile powders, granules or tablets which may contain diluents, dispersing and surface active agents, binders and lubricants.

It has also been found that the cinnamamide of formula (IA), preferably the trans configuration thereof, decreases muscle tone in mammals and thus is useful as a muscle relaxant.

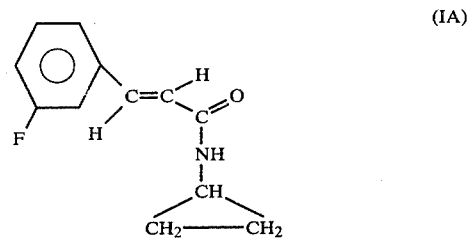

The compound of formula (IA) may be made by any method known for the synthesis of cinnamamides of analogous structure. For example, it may be prepared by the acylation of cyclopropylamine by the corresponding acid, trans-3-fluoro cinnamic acid, or a reactive derivative thereof such as a thioester, an ester, an amide, an acid halide or an acid anhydride. A wide variety of reaction conditions may be employed depending upon the nature of the acylating agent, but in general the reactants may be refluxed together, preferably in an inert liquid medium such as ether, benzene, toluene or cyclohexane.

A most convenient method of synthesis is to react the acid chloride with the amine.

Preferably one equivalent of the halide should be used with two or more equivalents of the amine, but the molar excess of the amine may be replaced by another base such as triethylamine, pyridine, dimethylaniline, or potassium or sodium carbonate. A wide variety of polar or non-polar liquid media may be used including water, alkanols such as methanol, ethanol, ether, dioxane, benzene, toluene, xylene, petroleum ether, cyclohexane, tetrahydrofuran, chloroform and carbon tetrachloride. A wide range of temperature conditions may be employed, for example from $-10°$ C. to the reflux temperature of the reaction mixture.

Trans-3-fluorocinnamic acid may be made by classical organic synthetic methods such as the Perkin synthesis, the Reformatsky reaction and the Knoevenagel condensation.

The compound of formula (IA) may be used to decrease the muscle tone of mammals, including man. For example it may be used to induce relaxation of skeletal muscle in the treatment or prophylaxis of spastic, hypertonic and hyperkinetic conditions associated with disorders due to increased skeletal muscle tone. In particular the compound may be used in the treatment and symptomatic relief of conditions such as parkinsonism, chorea, arthritis, athetosis, status epilepticus and tetanus and especially in the relief of muscle spasm in conditions such as myositis, spondylitis cerebral palsy and multiple sclerosis.

The compound of formula (IA) may preferably be administered to decrease muscle tone e.g., as a muscle relaxant to suppress polysynaptic reflex contractions at a dose of 2 to 200/mg/kg of bodyweight per day. The optimum dose of course will vary with the nature of the disease, the condition of the patient and the route of administration, but the preferred dose range is of 20 to 60 mg/kg, most conveniently 30 to 50 mg/kg body weight, per day. Administration of the desired daily dose is preferably in three divided doses. For example, convenient forms of administration include tablets each containing from 100 to 500 mg of the compound of formula (IA).

For use in medicine the compound of formula (IA) may be administered as a pure chemical but is preferably presented with an acceptable carrier therefor as a pharmaceutical composition. The carrier must of course be 'acceptable' in the sense of being compatible with the other ingredients of the composition and not deleterious to the recipient of the composition. The carrier may be a solid or a liquid or a mixture of solid and liquid substances, and is preferably formulated with the compound of formula (IA) as a unit dose composition, for example a tablet, capsule or cachet for oral administration or a suppository for rectal administration. Other pharmaceutically active substances may also be present in compositions of the present invention, and the composition may be formulated by any of the well-known techniques of pharmacy consisting basically of admixture of its components. Unit-dose compositions, for oral, rectal or parenteral administration (vid. inf.), conveniently contain the compound of formula (IA) in an amount in the range 100 to 500 mg.

For oral administration, fine powders or granules of the compound may contain diluents and dispersing and surface active agents, and may be presented in a draught in water or in a syrup; in capsules or cachets in the dry state or in an aqueous or non-aqueous suspension, when a suspending agent may also be included; in tablets, preferably made from granules of the active ingredient with a diluent, by compression with binders and lubricants; or in a suspension in water or a syrup or an oil or in a water/oil emulsion, when flavouring, preserving, suspending, thickening and emulsifying agents may also be included. The granules or the tablets may be coated, and the tablets may be scored. For parenteral administration (by intramuscular or intraperitoneal injection), the compound may be presented in unit-dose or multi-dose containers in aqueous or nonaqueous injection solutions which may contain antioxidants, buffers, bacteriostats and solutes which render the compound isotonic with the blood; or in aqueous or non-aqueous suspensions when suspending agents and thickening agents may also be included; extemporaneous injected solutions and suspensions may be made from sterile powders, granules or tablets which may contain diluents, dispersing and surface active agents, binders and lubricants.

It will be understood from the foregoing description that what we will claim in accordance with this invention comprises any novel feature described herein, principally but not exclusively as follows:

(a) Novel compounds of formula (I or IA) hereinabove defined.

(b) Novel compounds of formula (I or IA) hereinabove defined having the trans configuration.

(c) The synthesis of a novel compound of formula (I or IA) by any known method and in particular the methods specifically described above and including the reaction of an acid m—X—PhCH=CHCO$_2$H or a reactive derivative thereof with a compound of the formula R.NH.W wherein W is a leaving group and R and X have the meaning in formula (I or IA).

(d) A pharmaceutical composition comprising a compound of formula (IA) and a pharmaceutically acceptable carrier therefor.

(e) A method for the treatment or prophylaxis of convulsion of a mammal comprising the administration to the mammal of an anti-convulsant effective, non-toxic amount of a compound of formula (IA).

(f) A composition and method for relaxing muscles e.g., skeletal muscles comprising a composition and method for administration of 3-fluoro-N-cyclopropylcinnamamide to a mammal e.g., man, in a non-toxic effective muscle relaxant amount (preferably having the trans configuration).

(g) A method of decreasing muscle tone in a mammal comprising the administration to the mammal of a muscle tone-decreasing effective, non-toxic amount of the compound of formula (IA) and preferably the trans configuration of the compound of formula (IA).

(h) A method of supressing polysynaptic reflex contractions in a mammal which comprises the administration to a mammal of an effective polysynaptic reflex contraction amount of a compound of formula (IA) and preferably the trans configuration thereof. The amount of compound for this purpose would preferably be at a daily dose of 2 to 200 mg/kg bodyweight and a unit dose for man would be 100 to 500 mg.

The following Examples illustrate the present invention but should not be construed as in any way constituting a limitation thereof. All temperatures are in degrees Celsius.

EXAMPLE 1

Trans 3-Bromo-N-cyclopropylcinnamamide

A mixture of trans 3-bromocinnamic acid (m.p. 177°–179° C.; 11.4 g), thionyl chloride (11.9 g) and dry benzene (150 ml) was heated at reflux for 2 hours. Solvent and excess thionyl chloride were removed by distillation under reduced pressure leaving trans 3-bromocinnamoyl chloride (12.2 g), b.p. 100°–100.5° C./0.2 mm Hg.

A solution of trans 3-bromocinnamoyl chloride (12.2 g) in dry toluene (150 ml) was added dropwise (rapidly) with rapid stirring to a solution of cyclopropylamine (6.3 g) in dry toluene (150 ml). The reaction mixture was stirred at room temperature for 2 hours, then at 30°–35° C. for an additional hour; and the solvent and excess amine were removed under reduced pressure. The residue was triturated with water to remove cyclopropylamine hydrochloride. The product was filtered, washed with dilute hydrochloric acid and then with water. It was then recrystallized from ethanol:water (1:10) to give white crystalline trans 3-bromo-N-cyclopropylcinnamamide (12 g), m.p. 110°–111° C. Elemental analysis, NMR and IR data were all consistent with the assigned structure. TLC gave one spot run on silica gel with 5:1 and with 3:1 hexane:ethanol.

EXAMPLE 2

Trans 3-Fluoro-N-cyclopropylcinnamamide

A mixture of 3-fluorobenzaldehyde (40 g), malonic acid (47 g), and an ethanolic solution (150 ml) containing pyridine (10 g) and piperidine (5 g) was heated at reflux with stirring for 8 hours. The reaction mixture was chilled and water (300 ml) was added, giving crystalline trans 3-fluorocinnamic acid which was removed by filtration, washed with water and dried. The trans 3-fluorocinnamic acid, m.p. 162°–163° C., was obtained in 84% yield (44.6 g).

A mixture of trans 3-fluorocinnamic acid (32.3 g), thionyl chloride (48 g) and dry benzene (300 ml) was heated at reflux for 2 hours. Solvent and excess thionyl chloride were removed by distillation under reduced pressure leaving trans 3-fluorocinnamoyl chloride (34 g) as an oil. A solution of trans 3-fluorocinnamoy chloride (3.3 g) in dry toluene (100 ml) was added with stirring to a solution of cyclopropylamine (2.5 g) in dry ether (100 ml) at ambient temperature. The reaction mixture was heated at 30°–34° C. for 2 hours, and the solvent and excess amine were removed under reduced pressure. The residue was triturated with water, filtered and recrystallized from ethanol:water (1:10) to give trans 3-fluoro-N-cyclopropylcinnamamide (3.3 g), m. p. 90°–91° C.

Elemental analysis, NMR and IR confirmed the structure. TLC gave one spot run on silica gel with 5:1 and, with 3:1 hexame: ethanol.

EXAMPLE 3

Trans 3-Trifluoromethyl-N-Cyclopropylcinnamamide

Using a method analogous to that described in Examples 2 and 3,3-trifluoromethylcinnamoyl chloride was reacted with cyclopropylamine to give trans 3-trifluoromethyl-N-cyclopropylcinnamamide, m.p. 98° C.

EXAMPLE 4

A suppository was formulated from the following ingredients:
trans 3-bromo-N-cyclopropylcinnamamide: 300 mg
cocoa butter: 2000 mg

EXAMPLE 5

A suppository was formulated from the following ingredients:
trans 3-fluoro-N-cyclopropylcinnamamide: 300 mg
cocoa butter: 2000 mg

EXAMPLE 6

A soft gelatin capsule was filled with the following ingredients:
trans 3-bromo-N-cyclopropylcinnamamide: 300 mg
lactose: 75 mg
starch, corn: 20 mg
fused silica: 2 mg
magnesium stearate: 3 mg

EXAMPLE 7

A soft gelatin capsule was filled with the following ingredients:
trans 3-fluoro-N-cyclopropylcinnamamide: 300 mg
lactose: 75 mg
starch, corn: 20 mg
fused silica: 2 mg
magnesium stearate: 3 mg

EXAMPLE 8

A syrup suspension was prepared from the following ingredients:
trans 3-bromo-N-cyclopropylcinnamamide: 300 mg
sodium carboxymethylcellulose: 20 mg
microcrystaline cellulose: 100 mg
glycerin: 500 mg
Polysorbate 80: 10 ml
flavoring agent: q.s.
preserving agent: 0.1%
sucrose syrup: q.s. to 5 ml

EXAMPLE 9

A compressed tablet was prepared from the following ingredients:
trans 3-fluoro-N-cyclopropylcinnamamide: 300 mg
starch, corn: 50 mg
microcrystalline cellulose: 50 mg
stearic acid: 4 mg
magnesium stearate: 1 mg
fused silica: 1 mg

EXAMPLE 11

A compressed tablet was prepared from the following ingredients:
trans 3-fluoro-N-cyclopropylcinnamamide: 300 mg
starch, corn: 50 mg
microcrystalline cellulose: 50 mg
stearic acid: 4 mg
magnesium stearate: 1 mg
fused silica: 1 mg

EXAMPLE 12

A suppository was formulated from the following ingredients:
trans 3-trifluoromethyl-N-cyclopropyl-cinnamamide: 300 mg
cocoa butter: 2000 mg

EXAMPLE 13

A soft gelatin capsule was filled with the following ingredients:
trans 3-trifluoromethyl-N-cyclopropylcinnamamide: 300 mg
lactose: 75 mg
starch, corn: 20 mg
fused silica: 2 mg
magnesium stearate: 3 mg

EXAMPLE 14

A syrup suspension was prepared from the following ingredients:
trans 3-trifluoromethyl-N-cyclopropylcinnamamide: 300 mg
sodium carboxymethylcellulose: 20 mg
microcrystalline cellulose: 100 mg
glycerin: 500 mg
Polysorbate 80: 10 ml
flavoring agent: q.s.
preserving agent: 0.1%
sucrose syrup: q.s. to 5 ml.

EXAMPLE 15

A compressed tablet was prepared from the following:
trans 3-trifluoromethyl-N-cyclopropylcinnamamide: 300 mg
starch, corn: 50 mg
microcrystalline cellulose: 50 mg
stearic acid: 4 mg
magnesium stearate: 1 mg
fused silica: 1 mg

EXAMPLE 16

In the MES pharmacological test referred to hereinbefore, the stated compounds had the given $ED_{50}$ when administered i.p. to mice or rats as appropriate.

| Compound | $ED_{50}$ (mg/kg) |
| --- | --- |
| trans 3-fluoro-N-cyclopropyl cinnamamide | 60 (mice) |
| trans 3-bromo-N-cyclopropylcinnamamide | 77 (mice) |
| trans 3-trifluoromethyl-N-cyclopropylcinnamamide | 56 (rat) |

EXAMPLE 17

Muscle Relaxant Activity

The effect of trans 3-fluoro-N-cyclopropylcinnamamide as a centrally acting muscle relaxant was determined using a method based on that described in Berger, F. M. & Bradley, W. (Br. J. Pharmac. Chemother, (1946), 1, 265–272) and Crankshaw, D. P. & Raper, C. (Br. J. Pharmac. (1970), 38, 148–156). At an oral dose of from 100–150 mg/kg the compound suppressed polysynaptic reflex contractions in the cat without affecting the monosynaptic kneed-jerk reflex.

EXAMPLE 18

Trans 3-chloro-N-cyclopropylcinnamamide

A solution of 3-chlorocinnamoyl chloride (6 g) in dry tolune (100 ml) was added with stirring to a solution of cyclopropylamine (6 g) in dry benzene (50 ml). The reaction mixture was allowed to stand at room temperature overnight, and the solvent was evaporated under reduced pressure. The residue was thoroughly triturated with water containing a small amount of sodium carbonate, washed with water and filtered. Recrystallization of the resulting crude product from ethanol-water (1:10) gave trans 3-chloro-N-cyclopropylcinnamamide (5 g), m.p. 112°–113° C. Elemented analysis, nmr and ir data were all consistent with the assigned structure. TLC gave one spot run on silica gel with 5:1 and with 3:1 hexane:ethanol.

EXAMPLE 19

A compressed tablet is prepared from the following ingredients:
trans 3-chloro-N-cyclopropylcinnamamide: 300 mg
starch, corn: 50 mg
microcrystalline cellulose: 50 mg stearic acid: 4 mg
magnesium stearate: 1 mg
fused silica: 1 mg

EXAMPLE 20

A syrup suspension is prepared from the following ingredients:
trans 3-chloro-N-cyclopropylcinnamamide: 300 mg
sodium carboxymethycellulose: 20 mg
microcrystalline cellulose: 100 mg
glycerin: 500 mg
polysorbate 80: 0.10 ml
flavoring agent: q.s.
preserving agent: 0.1%
sucrose syrup: q.s. to 5 ml

EXAMPLE 21

A soft gelatin capsule is filled with the following ingredients:
trans 3-chloro-N-cyclopropylcinnamamide: 300 mg
lactose: 75 mg
starch, corn: 20 mg
fused silica: 2 mg
magnesium stearate: 3 mg

EXAMPLE 22

A suppository is formulated from the following ingredients:
trans 3-chloro-N-cyclopropylcinnamamide: 300 mg
cocoa butter: 2000 mg

What I claim is:

1. Trans 3-fluoro-N-cyclopropylcinnamamide.

2. A pharmaceutical composition for use as a skeletal muscle relaxant comprising a non-toxic effective skeletal muscle relaxing amount of trans 3-fluoro-N-cyclopropylcinnamamide and a pharmaceutically acceptable carrier therefore.

3. The composition of claim 2 in which the amount is 100 to 500 mg.

4. The composition of claim 2 in which the composition is in unit dose form.

5. The composition of claim 2 in which the composition is suitable for oral, parenteral or rectal administration.

6. The composition of claim 2 in the form of a tablet.

7. The composition of claim 2 in the form of a capsule.

8. A pharmaceutical composition in unit dose form comprising 100 to 500 mg of trans3-fluoro-N-cyclopropylcinnamamide and a pharmaceutically acceptable carrier therefore.

9. The composition of claim 8 in the form of a tablet or capsule.

10. The composition of claim 8 in a form for oral administration.

11. A method for the treatment or prophylaxis of increased muscle tone of a mammal which comprises administration to said mammal of a non-toxic effective tone decreasing amount of trans-3-fluoro-N-cyclopropylcinnamamide.

12. A method as claimed in claim 11 in which trans-3-fluoro-N-cyclopropylcinnamamide is administered orally.

13. A method as claimed in claim 11 in which trans-3-fluoro-N-cyclopropylcinnamamide is administered parenterally.

14. A method as claimed in claim 11 in which the mammal is man.

15. A method as claimed in claim 11 in which the administered amount is from 2 to 200 mg/kg of body weight of the mammal.

16. A method as claimed in claim 11 in which the administered amount is from 20 to 60 mg/kg of body weight of the mammal.

17. The method of claim 11 in which the amount is 100 to 500 mg.

18. The method of claim 17 in which the mammal is man.

19. The method of claim 17 in which the compound is administered orally.